US012465734B2

(12) United States Patent
Bain

(10) Patent No.: US 12,465,734 B2
(45) Date of Patent: Nov. 11, 2025

(54) RESILIENT ADHESIVE SHEATH FOR USE WITH DILATION DEVICE

(71) Applicant: Growth Armor, LLC, Wilmington, DE (US)

(72) Inventor: Michael A. Bain, Costa Mesa, CA (US)

(73) Assignee: Growth Armor, LLC, Wilmington, DE (US)

( * ) Notice: Subject to any disclaimer, the term of this patent is extended or adjusted under 35 U.S.C. 154(b) by 551 days.

(21) Appl. No.: 17/931,411

(22) Filed: Sep. 12, 2022

(65) Prior Publication Data

US 2024/0082552 A1 Mar. 14, 2024

(51) Int. Cl.
*A61M 29/00* (2006.01)
*A61M 25/00* (2006.01)

(52) U.S. Cl.
CPC ..... *A61M 29/00* (2013.01); *A61M 2025/0024* (2013.01)

(58) Field of Classification Search
CPC ............ A61H 19/44; A61H 2201/0207; A61H 2201/10; A61M 29/00; A61M 29/02; A61M 2025/0024; A61M 2025/1081
USPC ........................................................ 606/191
See application file for complete search history.

(56) References Cited

U.S. PATENT DOCUMENTS

| | | | | |
|---|---|---|---|---|
| 2,448,938 | A * | 9/1948 | Wayne .................... | A61F 13/10 604/355 |
| 5,169,386 | A | 12/1992 | Becker et al. | |
| 5,336,211 | A * | 8/1994 | Metz ........................ | A61F 5/453 604/352 |
| 6,635,078 | B1 | 10/2003 | Zhong et al. | |
| 7,963,285 | B2 * | 6/2011 | Attila ........................ | A61F 6/00 600/38 |
| 2004/0142024 | A1 * | 7/2004 | Chono ...................... | A61P 1/08 424/449 |
| 2009/0148503 | A1 * | 6/2009 | Trieu ..................... | A61B 17/42 424/447 |
| 2017/0239077 | A1 * | 8/2017 | Tang ......................... | A61F 6/04 |
| 2018/0000502 | A1 * | 1/2018 | Baym .................... | A61B 17/32 |

OTHER PUBLICATIONS

Internationl Search Report and Written Opinion for PCT/US23/32299; Jan. 23, 2024.

* cited by examiner

*Primary Examiner* — Jocelin C Tanner
(74) *Attorney, Agent, or Firm* — Stetina Garred Brucker & Newboles

(57) ABSTRACT

A resilient adhesive sheath for use in enhancing the durability and hygienic properties of a dilatation device is contemplated as an elongate tubular section being formed of a resiliently flexible material, with an adhesive layer disposed on its interior surface. A removable protective layer is disposed over the adhesive layer in order to preserve the adhesive properties prior to use and to prevent the adhesive from prematurely bonding. The resilient adhesive sheath is configured to transition from a compressed configuration while packaged to an extended configuration, in a manner similar to a conventional prophylactic condom. The protective layer may be removed from over the adhesive layer and the adhesive sheath subsequently placed over the insertion portion of the dilatation device with the adhesive layer in contact therewith to allow for the adherence thereto. The adhesive sheath may be subsequently removed and replaced with a new adhesive sheath.

19 Claims, 2 Drawing Sheets

RESILIENT ADHESIVE SHEATH FOR USE WITH DILATION DEVICE

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Technical Field

The present disclosure relates generally to the field of dilatation devices for therapeutic and recreational purposes. More particularly, the present disclosure relates to durable protective coverings for use with such devices.

2. Related Art

There are a number of reasons for which an individual may utilize a device configured for insertion into the vagina or anus. Medically, there are a number of disorders that involve the pelvic area, including of the bladder, vagina, pelvic floor muscle, rectum and cervix, for which insertion of devices for therapeutic treatment is a common method of treatment. Likewise, such devices are often used for sexual stimulation purposes. Notably, the disclosure of Applicant's prior filed U.S. patent application Ser. No. 17/655,761, entitled IMPROVED DILATATION DEVICE INCORPORATING INFLATABLE BALLOON, Applicant's prior filed U.S. patent application Ser. No. 17/809,357, entitled DILATATION DEVICES INCORPORATING ENHANCED FEATURES are important to complete understanding of the disclosure made herein, and accordingly, the entire disclosure of each is incorporated herein as if fully restated.

The pubococcygeal muscle, commonly called the pelvic floor muscle, is responsible for holding all the pelvic organs within the pelvic cavity. The pelvic floor muscle consists of a deep muscle layer and a superficial muscle layer that work together to keep the pelvic organs healthy and in good working order. The muscle is suspended at the base of the pelvis and wraps around the vagina and rectum. The pelvic floor muscles may become damaged or weakened through childbirth, lack of use, aging, illness, or as the collateral result of surgical procedures. One of the symptoms related to a weakening of these muscles is urinary incontinence.

Other pelvic disorders include chronic pelvic pain and vulvodynia (pelvic muscle dysfunction), which may sometimes be experienced by young adult women. These disorders may be caused by involuntary contractions (spasms) of the levator ani and perineal muscles. This condition, sometimes referred to as vaginismus or pelvic floor tension myalgia, may be accompanied by difficult and painful penetration of the vagina (dyspareunia), often resulting in pain and other difficulties which substantially reduce a woman's quality of life, not only with regard to the participating in and enjoyment of penetrative sexual intercourse, but also in other facts of life, such as in the use of menstrual products such as tampons or during routine procedures such as the use of speculums during gynecological examinations.

Dilatation devices are commonly prescribed for the treatment of such conditions, and generally include products such as vaginal dilators and Kegel exercisers. Similarly, dilatation devices for insertion into the anus may also be prescribed, for example, in order to aid in treatment of conditions such as anal stenosis, where treatment involves progressive stretching and acclimation of the rectum to an ideal size to improve comfort and function following ano-rectal procedures, such as following surgeries on the prostate or for hemorrhoids.

Similarly, dilatation devices are also used for the enhancement of sexual pleasure, and in this context, such devices generally are referred to as sex toys. There may also be substantial overlap between the structure and functionality of devices adapted for therapeutic and recreational uses, and in many cases, especially when a pelvic disorder may directly impact the ability to enjoy sexual intercourse and pleasure, a single device may be utilized for both purposes. Many types of sex toys are known. Some of the most popular sex toys are designed for vaginal or anal insertion, and include items such as dildos, prostate stimulators, anal plugs, etc. Many of these devices may also include other stimulatory elements, such as vibrating or rotating functionalities.

Conventional dilatation devices suffer from a number of deficiencies. For example, conventional treatment of vaginismus or anal stenosis typically entails the progressive insertion of a progressively larger sequence of dilators until the vagina or anus becomes acclimated to the desired size. It is therefore desirable to have improved dilatation devices which may, for example, provide adaptive forms of dilatation therapies, potentially even taking into consideration biofeedback mechanisms, in order to assist in user comfort and to eliminate the requirement for the use of a series of dilators. Likewise, similar deficiencies may exist in the field of sex toys, and consequently, overall sexual pleasure may be enhanced the application of similar techniques to produce improved sex toys for insertion.

Accordingly, Applicant has developed certain innovations in the field of dilatation devices, which allow for adaptive forms of dilatation therapy using a single complex device, where prior methods of treatment may require the use of a number of devices. Furthermore, it is envisioned that such devices may be suitable for use by treatment professions, such as a medical clinic. Accordingly, there is a need for protective and hygienic equipment for use with such devices which may reduce wear and tear and allow for hygienic non-consumptive use of such devices in clinical settings.

BRIEF SUMMARY

To solve these and other problems, a resilient adhesive sheath for use in enhancing the durability and hygienic properties of a dilatation device is contemplated as an elongate tubular section being formed of a resiliently flexible material, with an adhesive layer disposed on its interior surface. A removable protective layer is disposed over the adhesive layer in order to preserve the adhesive properties prior to use and to prevent the adhesive from prematurely bonding. The resilient adhesive sheath is configured to transition from a compressed configuration while packaged to an extended configuration, in a manner similar to a conventional prophylactic condom. The protective layer may be removed from over the adhesive layer and the adhesive sheath subsequently placed over the insertion portion of the dilatation device with the adhesive layer in contact therewith to allow for the adherence thereto. The adhesive sheath may be subsequently removed and replaced with a new adhesive sheath, such as in situations where the existing adhesive sheath has become worn out or damaged, or to allow for hygienic re-use of the dilatation device between uses or between users or patients.

According to one exemplary embodiment of a resilient adhesive sheath for use with a dilatation device, the resilient adhesive sheath may comprise an elongate tubular section having an open proximal end and a closed distal end, the elongate tubular section being formed of a resiliently flexible material and having opposed exterior and interior surfaces defining an exterior and an interior, an adhesive layer disposed on the interior of the elongate tubular section against at least a portion of the interior surface, and a protective layer disposed on the interior of the elongate tubular section over the adhesive layer, the protective layer being configured to be removable from the resilient adhesive sheath to expose at least a portion of the adhesive layer, wherein the elongate tubular section is transitionable from a compressed configuration to an expanded configuration, and wherein the protective layer is configured to remain disposed over the adhesive layer while in the compressed and expanded configuration and during the transition therebetween.

According to the exemplary embodiment of a resilient adhesive sheath for use with a dilatation device, the open proximal end of the elongate tubular section may include a sealing element adapted to at least partially secure the open proximal end over an insertion portion of a dilatation device.

According to various more particular embodiments of a resilient adhesive sheath for use with a dilatation device, in the adhesive layer may comprise a pressure-sensitive adhesive, or one or more of: a light-activated, thermo-activated, or magnetically-activated adhesive, or a drying adhesive, or at least one portion of a multi-part adhesive.

According to more particular embodiments of a resilient adhesive sheath for use with a dilatation device, the protective layer may include a projecting element for assisting a user in removing the protective layer being from the resilient adhesive sheath, and the protective layer is formed of an elastically deformable material or a non-elastically deformable material. According to further embodiments of the resilient adhesive sheath the protective layer may be configured to be removed from the resilient adhesive sheath via helical detachment.

Further contemplated are methods of using a resilient adhesive sheath with an insertion portion of a dilatation device. According to one exemplary embodiment, such a method may comprising the steps of (a) providing a resilient adhesive sheath comprising an elongate tubular section having an open proximal end and a closed distal end, the elongate tubular sheath section being formed of a resiliently flexible material and having opposed exterior and interior surfaces defining an exterior and an interior, an adhesive layer disposed on the interior of the elongate tubular section against at least a portion of the interior surface, and a protective layer disposed on the interior of the elongate tubular section over the adhesive layer, the protective layer being configured to be removable from the resilient adhesive sheath to expose at least a portion of the adhesive layer, wherein the elongate tubular section is transitionable from a compressed configuration to an expanded configuration, and wherein the protective layer is configured to remain disposed over the adhesive layer while in the compressed and expanded configuration and during the transition therebetween; (b) transitioning the resilient adhesive sheath to the expanded configuration; (c) removing the protective layer from the resilient adhesive sheath to expose at least a portion of the adhesive layer; (d) placing the resilient adhesive sheath over the insertion portion of the dilatation device with the adhesive layer in contact with one or more surfaces of the insertion portion; and (e) adhering the adhesive layer to the surface of the insertion portion.

According to additional embodiments of the herein contemplated methods, the open proximal end of the elongate tubular section may include a sealing element adapted to at least partially secure the open proximal end over an insertion portion of a dilatation device.

According to more particular embodiments of the herein contemplated methods, the adhesive layer provided in step (a) may comprise a pressure-sensitive adhesive, and step (e) of adhering the adhesive layer may comprise the application of pressure between the adhesive layer and the one or more surfaces of the insertion portion.

According to more particular embodiments of the herein contemplated methods, the adhesive layer provided in step (a) may comprise one or more of: a light-activated adhesive, a thermo-activated adhesive, or a magnetically-activated adhesive, and step (e) of adhering the adhesive layer to the surface of the insertion portion may comprise the application for a sufficient duration of one or more of: light at a sufficient wavelength, heat at a sufficient temperature, or a magnetic field at a sufficient flux.

According to more particular embodiments of the herein contemplated methods, the adhesive layer provided in step (a) may comprise a drying adhesive, and step (e) of adhering the adhesive layer to the surface of the insertion portion may comprise permitting the drying adhesive to dry for a sufficient duration of time.

According to more particular embodiments of the herein contemplated methods, the adhesive layer provided in step (a) may comprise at least one portion of a multi-part adhesive, and step (e) of adhering the adhesive layer to the surface of the insertion portion may comprise applying the other one or more portions of the multi-part adhesive to the adhesive layer or to the surface of the adhesive portion.

According to further embodiments of the herein contemplated methods, the protective layer may include a projecting element for assisting a user in removing the protective layer from the resilient adhesive sheath, and wherein step (c) of removing the protective layer from the resilient adhesive sheath to expose at least a portion of the adhesive layer comprises gripping of the projecting element.

The herein contemplated methods further envision that the protective layer may be formed of an elastically deformable material, and during step (b) of the transitioning the resilient adhesive sheath to the expanded configuration, the protective layer may be configured to elastically deform so as to remain disposed over the adhesive layer, or that the protective layer may not be formed of an elastically deformable material, and during step (b) of the transitioning the resilient adhesive sheath to the expanded configuration, the protective layer is configured to remain disposed over the adhesive layer without elastically deforming.

It is further contemplated that the in step (c) of removing the protective layer from the resilient adhesive sheath to expose at least a portion of the adhesive layer, this removing step may comprise detaching the protective layer from the resilient adhesive sheath via a helical procession.

The present disclosure will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION

According to various aspects of the present disclosure, a resilient adhesive sheath for use in enhancing the durability and hygienic properties of a dilatation device is contemplated as an elongate tubular section being formed of a resiliently flexible material, with an adhesive layer disposed on its interior surface. A removable protective layer is disposed over the adhesive layer in order to preserve the adhesive properties prior to use and to prevent the adhesive from prematurely bonding. The resilient adhesive sheath is configured to transition from a compressed configuration while packaged to an extended configuration, in a manner similar to a conventional prophylactic condom. The protective layer may be removed from over the adhesive layer and the adhesive sheath subsequently placed over the insertion portion of the dilatation device with the adhesive layer in contact therewith to allow for the adherence thereto. The adhesive sheath may be subsequently removed and replaced with a new adhesive sheath, such as in situations where the existing adhesive sheath has become worn out or damaged, or to allow for hygienic re-use of the dilatation device between uses or between users or patients.

Figure 1:
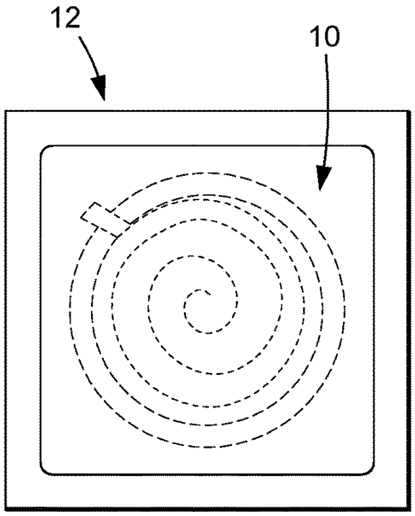
FIG. 1 is a frontal cutaway view illustrating a resilient adhesive sheath in a compressed configuration within a storage package according to an exemplary embodiment of the present disclosure.

Turning now to FIG. 1, a is a frontal cutaway view illustrating a resilient adhesive sheath 10 in a compressed configuration within a storage package 12 according to an exemplary embodiment of the present disclosure is shown.

As may be seen, a resilient adhesive sheath 10 in a compressed configuration may be packaged within a storage package 12 in a manner similar to a conventional prophylactic condom, with the material of the elongate tubular section 14 being rolled, folded, squeezed, or otherwise compressed along a longitudinal axis into a generally convenient planar form and sealed within an airtight package. However, it may also be seen that a resilient adhesive sheath need not be compressed along a longitudinal axis in order to be in a compressed configuration, but also may be compressed in other ways, such as compressed along other axes or flattened along a non-longitudinal axis and optionally rolled to form a cylinder, as desired. It may be seen that the exact form of the compressed configuration of the resilient adhesive sheath 10 may not be of critical importance, as long as the form is useful for maintaining the physical and hygienic integrity of the of the resilient adhesive sheath 10 prior to use, which will generally (but not necessarily) be achieved by containing the resilient adhesive sheath 10 in its compressed configuration within a sterile packaging material, such as a sterile foil pouch as commonly utilized in the medical device or food packaging industry.

Figure 2:
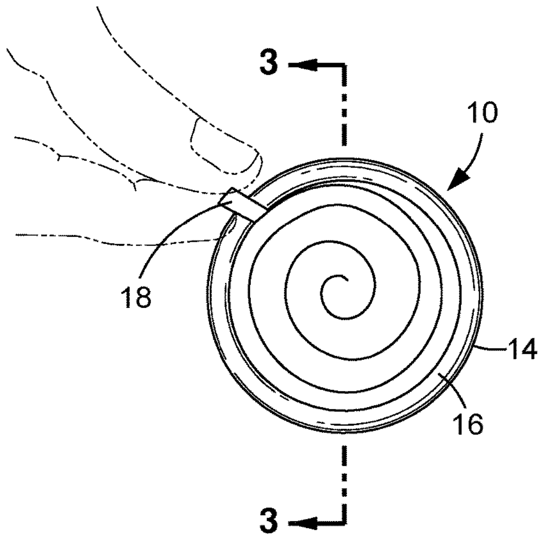
FIG. 2 is a front view illustrating a resilient adhesive sheath in a compressed configuration according to an exemplary embodiment of the present disclosure.

Turning now to FIG. 2, a front view illustrating a resilient adhesive sheath in a compressed configuration according to an exemplary embodiment of the present disclosure is shown.

As may be seen, a resilient adhesive sheath 10 in a compressed configuration may be configured to have a similar size and configuration as a conventional prophylactic condom, and may bear an eternal externally resemblance thereto. A resilient adhesive sheath 10 will generally comprise an elongate tubular member 14 having an open proximal end 22 and a closed distal end 24. As may be recognized, it is desirable that the elongate tubular member may be formed of a resiliently flexible material configured to elastically deform without breaking or substantially degrading, and in many cases may utilize similar materials to a conventional prophylactic condom for this purpose, such as latex, polyurethane, or polyisoprene. However, it may be seen that other materials may be utilized which may have differing properties of flexibility, toughness, and elastic deformability, without departing from the scope or spirit of the present disclosure. It should be recognized, however, that just as the general purpose of a condom is to serve as a barrier to the passage of bodily fluids, and that any material may be utilized which at least partially accomplish this purpose, so to here the primary purpose of the present resilient adhesive sheath 10 may also to be in part to prevent the passage of bodily fluids to an enhanced dilatation device upon which the resilient adhesive sheath 10 is placed, such that the enhanced dilatation device remains in a generally hygienic condition, and as such, the materials which may be judged suitable for this purpose may be guided by these and other objectives.

The elongate tubular member 14 may have opposed exterior and interior surfaces defining an exterior and an interior. In the exemplary embodiment illustrated, the elongate tubular member 14 is formed of a single layer of material. However, it may also be seen that laminates or other forms of multi-layered materials may be utilized to form the elongate tubular member 14, without departing from the scope and spirit of the present disclosure. Furthermore, it may be seen that, similar to a conventional prophylactic condom, the elongate tubular member 14 as described herein may be readily inverted into an inside-out configuration, such that the internal surface becomes external, and vice-versa, and that it may be desirable to perform such an inversion, for example, for purposes of more easily attaching and adhering the elongate tubular member 14 to an insertion portion of an enhanced dilatation device. Therefore, the terms used herein shall remain consistent and shall define the "interior surface" as the surface against which the adhesive layer is disposed and which is intended to be interior to the resilient adhesive sheath 10 when it is in the expanded configuration and adhered to the insertion portion of a dilatation device, regardless of whether the elongate tubular member 14 is inside-out or not, or in the expanded or compressed configuration. Likewise, the "exterior surface" shall consistently refer to the surface opposed to said interior surface, and further, terms such as "interior" and "exterior" are made in reference to the orientation of the device while in the expanded configuration and adhered to the insertion portion of a dilatation device.

Disposed on the interior of the elongate tubular section 14, against at least a portion of the interior surface, is an adhesive layer 20. The adhesive layer 20 may be any adhesive configured to adhere the resilient adhesive sheath 10 over the insertion portion of the dilatation device. In the exemplary embodiment, the adhesive layer comprises a pressure-sensitive adhesive. However, in other embodiments, the adhesive layer may comprise one or more of a light activated adhesive, such as a UV-activated adhesive, a thermo-activated adhesive, or a magnetically-activated adhesive. In further embodiments, the adhesive layer 20 may comprise a drying adhesive. In still further embodiments, the adhesive layer may comprise or at least one portion of a multi-part adhesive, with the remaining portions being applied to the adhesive layer 20 or to the surface of the insertion portion of the dilatation device in order to activate the adhesive so that it may be adhered to the surface of the insertion portion of the dilatation device.

Disposed further interior to, and at least partially over the adhesive layer 20 is a protective layer 16, the protective layer 16 being configured to be removable from the resilient adhesive sheath 10 to at least partially expose the adhesive layer 20. As may be appreciated, the function of the protective layer 16 is to prevent the adhesive layer 20 from prematurely adhering to surfaces or materials prior to the application of the resilient adhesive sheath to the dilatation device, and to preserve the adhesive qualities of the adhesive layer 20. In this regard, it is contemplated that the protective layer 16, or at least the portion of the protective layer 16 contacting the adhesive layer 20, be formed of a material which will not tend to permanent adhere to the adhesive layer 20, but rather be formed of a material configured to preserve the adhesive qualities of the adhesive layer 20, which may by simply serving as a physical barrier, but may also be through chemical or material properties which may preserve the adhesive qualities of the adhesive layer 20, such as via the preventing of the passage of atmospheric components or portions of the electromagnetic spectrum to the adhesive layer 20 which may result in an activation or curing of the adhesive material contained therein, such as atmospheric moisture or UV light. Suitable materials may include, without limitation, plastic or metallic films, polymers, impregnated parchments or papers such as waxed paper, etc. It should be appreciated that the exact material identity of the protective layer 16 may be chosen from many potential materials, and the exact identity of the particular material may depend on the particular objectives of the construction and other materials utilized for the resilient adhesive sheath 10, such as the elongate tubular member 14 or the adhesive layer 20, and that the use of any material for the protective layer 16 which achieves the objectives described herein should be considered within the scope and spirit of the present disclosure, including future developed materials.

It may be seen that the protective layer may also include a projecting element 18 for assisting a user in removing the protective layer 16 from the resilient adhesive sheath 14 so as to expose at least a portion of the adhesive layer 20. In the exemplary embodiment, the projecting element 18 comprises a tab attached near to the open proximal end 22 of the elongate tubular section 14, which may be grasped in order to allow for the removal of the protective layer 16 without the user needing to reach into the interior of the elongate tubular section 14. However, it may be seen in other embodiments that other projecting elements 18 may be utilized. For example, it may be readily conceived that the projecting element 18 may comprise, for example but without limitation, one or more pull-strings attached at one or more locations to the protective layer 16, such as at the distal end, which may permit a user to pull the pull-string in order to begin removal of the protective layer starting at the distal end, rather than at the proximal end, which might be preferable according to certain embodiments. The exact qualities and of the projecting element 18 may thus be seen to vary, and therefore, the use of different types of different structural elements having different configurations to accomplish the purpose of the projecting element 18 (assisting in the ease of removal of the protective layer 16) which achieves the objectives described herein should be considered within the scope and spirit of the present disclosure.

Figure 3:
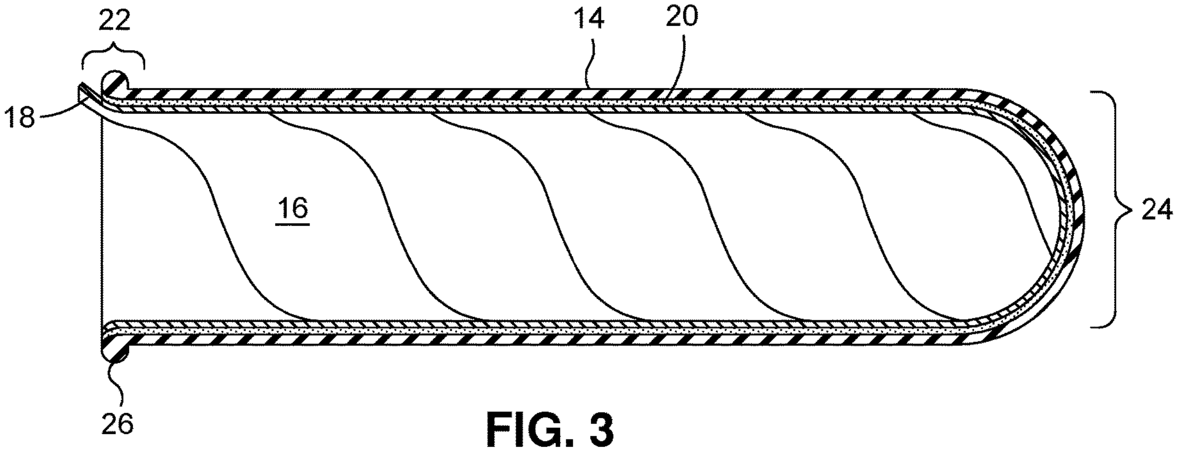
FIG. 3 is a side cross-sectional view illustrating a resilient adhesive sheath in an expanded configuration according to an exemplary embodiment of the present disclosure.

Turning now to FIG. 3, a side cross-sectional view illustrating a resilient adhesive sheath 10 in an expanded configuration according to an exemplary embodiment of the present disclosure is shown.

Figure 4:
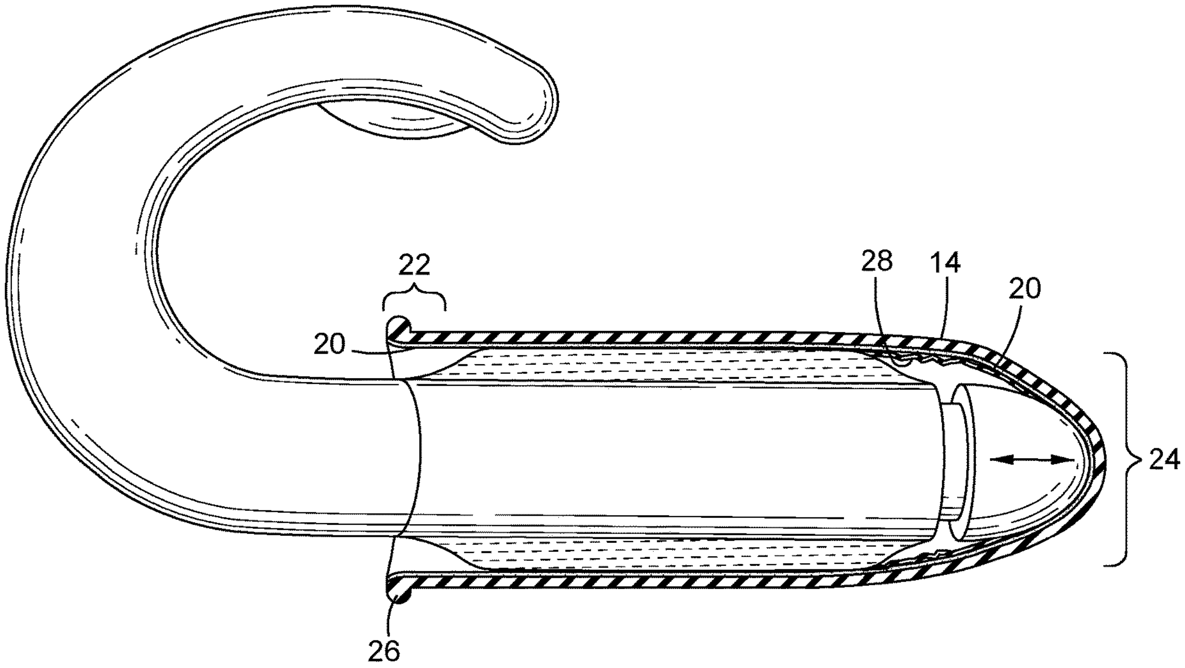
FIG. 4 is a side cross-sectional view illustrating a resilient adhesive sheath in an expanded configuration placed over the insertion portion of the dilatation device according to an exemplary embodiment of the present disclosure.

As may be seen, in the expanded configuration, the resilient adhesive sheath 10 may be ready for placement over the over the insertion portion of the dilatation device, as is illustrated in FIG. 4. It may also be seen how the relatively planar form of the resilient adhesive sheath 10 while in the compressed configuration may be expanded to the expanded configuration via extension along the longitudinal axis running from the open proximal end 22 to the closed distal end 24 according to various methodologies, including, for example, simple accordion-style lateral expansion, an unfolding motion, or a toroidal "rolling" action similar to the manner in which conventional prophylactic condom are typically compressed and expanded into an expanded form.

It may also be seen that the open proximal end 22 may include a sealing element 26 adapted to at least partially secure the open proximal end over an insertion portion of a dilatation device. The sealing element 26 may be any structure or component thereof which is adapted to function so as to at least partially assist in maintaining at least a portion of the open proximal end 22 in position on the insertion portion of the dilatation device. In the embodiment illustrated in FIG. 3, the sealing element 26 comprises a rim at the open proximal end 22 which may be seen to exert a more substantial force of elasticity than the remainder of the material of the elongate tubular section 14 owing to its greater thickness. However, in other embodiments, it may be seen that the sealing element 26 may be other structures or components of structures, which may or may not be subsidiary components of the elongate tubular section 14 or other components of the resilient adhesive sheath 10. For example, it may be seen that the sealing element may, in other embodiments, be an entirely separate structure that attaches over or under the elongate tubular section 14 proximate to the open proximal end 26. Many types of structures or components of structures are envisioned as capable of being adapted to perform the function of the sealing element 26, including bands, straps, tensioners, etc., and it may be seen that the exact identity of the structure which performs the function of the sealing element 16 may not necessarily be critical to the scope and spirit of the present disclosure, as long as its function of at least partially assisting in maintaining at least a portion of the open proximal end 22 in position on the insertion portion of the dilatation device. It may thus be further seen that the structure which performs this function may also serve a further purpose in addition, such as serving as an attachment or mounting point for another component, such as a strap which also maintains a separate device, such an enhanced stimulatory device, in a proper position in relation to the resilient adhesive sheath 10 or the dilatation device.

As may be further seen by FIG. 3, the protective layer disposed on the interior of the elongate tubular section 14 over the adhesive layer 20, the protective layer 16 may be configured to be removable from the resilient adhesive sheath 10 to expose at least a portion of the adhesive layer 20 via being configured to detach in a helical manner, which may be realized by, among other things, the protective layer 16 being formed as a strip attached in a helical fashion to the interior of the elongate tubular section 14, or being formed with pre-formed perforations or other mechanisms designed to allow the protective layer 16 to separate and detach from the resilient adhesive sheath 10 in a helical fashion. It may be appreciated that this method of attachment/detachment may have certain benefits in both ease of removal and of the protective layer 16, and in ease of transition from a compressed to an expanded configuration. It may be further seen that such a helical configuration of the protective layer 16 may permit the use of materials for the protective layer 16 which may or may not be an elastically deformable material, whereas other configurations may require the use of an elastically deformable material in order to prevent the formation of regions of self-adhesion or unintended detachment during the process of transition to the expanded configuration. Further, in a configuration where the protective layer 16 may be removed, for example, by beginning at the closed distal end 24 outward, such a configuration may permit the user to grasp the exterior of the closed distal end 24 of the elongate tubular sheath 14 with one hand, and grasp a projecting element (i.e. a string) attached to the protective layer 16 proximal to the closed distal end within the interior of the elongate tubular section 14, and to pull in opposite direction to helically detach the entire protective layer 16 into a single strip of material using one motion, which may allow for significant ease of use. However, it may be seen that in other embodiments, such as the illustrated exemplary embodiment, other configurations are possible, all of which should be considered within the scope and spirit of the present disclosure.

Turning now to FIG. 4, a side cross-sectional view illustrating a resilient adhesive sheath in an expanded configuration placed over the insertion portion of the dilatation device according to an exemplary embodiment of the present disclosure is shown.

As may be appreciated, a method of using the resilient adhesive sheath 10 as presently disclosed may be realized by, following the removal of the protective layer 16 to expose at least a portion of the adhesive layer 20, by placing the resilient adhesive sheath 10 over one or more surfaces 28 of the insertion portion of the dilatation device, and adhering the adhesive layer 20 to the surface of the insertion portion according the particular nature of the adhesive utilized in the adhesive layer 20 and the other characteristics of the resilient adhesive sheath 10.

It may thus be appreciated why it may be important that the resilient adhesive sheath 10 may be formed of an elastically resilient material, in that the enhanced dilation devices as contemplated by Applicant's earlier filed U.S. patent application Ser. No. 17/655,761, entitled IMPROVED DILATATION DEVICE INCORPORATING INFLATABLE BALLOON, Applicant's prior filed U.S. patent application Ser. No. 17/809,357, entitled DILATATION DEVICES INCORPORATING ENHANCED FEATURES may incorporate features which allow for the expansion or other forms of motion of the underlying surfaces of the dilatation devices along multiple planes and axes, and as such, should be elastically resilient to accommodate such motion without ripping or otherwise weakening as a result of such motion. Likewise, it may be seen that it may be desirable, in certain embodiments, to form the protective layer 16 of a material having a similar modulus of elasticity as the elongate tubular section 14 so that, prior to the removal of the resilient adhesive sheath, the protective layer may be less prone to detach in an unintended fashion upon application of force to the elongate tubular section 14 which may result in a shearing action vis-à-vis the protective layer 16. However, it may be seen that by configuring the detachable protective layer 16 in certain configurations, such as via a helical configuration as depicted in the exemplary embodiment, even the use of a non-elastically deformable material for the protective layer 16 in conjunction with an highly flexible or elastic elongate tubular section may mitigate the likelihood of unintended detachment.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the exemplary embodiments.

What is claimed is:

1. A resilient adhesive sheath for use with a dilation device, the resilient adhesive sheath comprising:

an elongate tubular section having an open proximal end and a closed distal end, the elongate tubular section being formed of a resiliently flexible material and having opposed exterior and interior surfaces defining an exterior and an interior;

an adhesive layer disposed on the interior of the elongate tubular section against at least a portion of the interior surface; and a protective layer disposed in a helical fashion to the interior of the elongate tubular section over the adhesive layer, the protective layer being configured to be removable from the resilient adhesive sheath to expose at least a portion of the adhesive layer, the protective layer being configured to be removable from the resilient adhesive sheath via helical detachment;

wherein the elongate tubular section is transitionable from a compressed configuration to an expanded configuration, and wherein the protective layer is configured to remain disposed over the adhesive layer while in the compressed and expanded configuration and during the transition therebetween.

2. The resilient adhesive sheath of claim 1, wherein the open proximal end of the elongate tubular section includes a sealing rim adapted to at least partially secure the open proximal end over an insertion portion of a dilatation device.

3. The resilient adhesive sheath of claim 1, wherein the adhesive layer comprises a pressure-sensitive adhesive.

4. The resilient adhesive sheath of claim 1, wherein the adhesive layer comprises one or more of: a light-activated, thermo-activated, or magnetically-activated adhesive.

5. The resilient adhesive sheath of claim 1, wherein the adhesive layer comprises a drying adhesive.

6. The resilient adhesive sheath of claim 1, wherein the adhesive layer comprises at least one portion of a multi-part adhesive.

7. The resilient adhesive sheath of claim 1, wherein the protective layer includes a projecting tab for assisting a user in removing the protective layer from the resilient adhesive sheath.

8. The resilient adhesive sheath of claim 1, wherein the protective layer is formed of an elastically deformable material.

9. The resilient adhesive sheath of claim 1, wherein the protective layer is formed of non-elastically deformable material.

10. A method of using a resilient adhesive sheath with an insertion portion of a dilatation device, the method comprising the steps of:

(a) providing a resilient adhesive sheath comprising an elongate tubular section having an open proximal end and a closed distal end, the elongate tubular section being formed of a resiliently flexible material and having opposed exterior and interior surfaces defining an exterior and an interior, an adhesive layer disposed on the interior of the elongate tubular section against at least a portion of the interior surface, and a protective layer disposed in a helical fashion to the interior of the elongate tubular section over the adhesive layer, the protective layer being configured to be removable from the resilient adhesive sheath via helical detachment to expose at least a portion of the adhesive layer, wherein the elongate tubular section is transitionable from a compressed configuration to an expanded configuration, and wherein the protective layer is configured to remain disposed over the adhesive layer while in the compressed and expanded configuration and during the transition therebetween;

(b) transitioning the resilient adhesive sheath to the expanded configuration;

(c) removing the protective layer from the resilient adhesive sheath via helical detachment to expose at least a portion of the adhesive layer;

(d) placing the resilient adhesive sheath over the insertion portion of the dilatation device with the adhesive layer in contact with one or more surfaces of the insertion portion; and (e) adhering the adhesive layer to the surface of the insertion portion.

11. The method of claim 10, wherein the wherein the open proximal end of the elongate tubular section includes a sealing element adapted to at least partially secure the open proximal end over an insertion portion of a dilatation device.

12. The method of claim 10, wherein the adhesive layer provided in step (a) comprises a pressure-sensitive adhesive, and wherein step (e) of adhering the adhesive layer comprises the application of pressure between the adhesive layer and the one or more surfaces of the insertion portion.

13. The method of claim 10, wherein the adhesive layer provided in step (a) comprises one or more of: a light-activated adhesive, a thermo-activated adhesive, or a magnetically-activated adhesive, and wherein step (e) of adhering the adhesive layer to the surface of the insertion portion comprises the application for a sufficient duration of one or more of: light at a sufficient wavelength, heat at a sufficient temperature, or a magnetic field at a sufficient flux.

14. The method of claim 10, wherein the adhesive layer provided in step (a) comprises a drying adhesive, and wherein step (e) of adhering the adhesive layer to the surface of the insertion portion comprises permitting the drying adhesive to dry for a sufficient duration of time.

15. The method of claim 10, wherein the adhesive layer provided in step (a) comprises at least one portion of a multi-part adhesive, and wherein step (e) of adhering the adhesive layer to the surface of the insertion portion comprises applying the other one or more portions of the multi-part adhesive to the adhesive layer or to the surface of the adhesive portion.

16. The method of claim 10, wherein the protective layer includes a projecting element for assisting a user in removing the protective layer from the resilient adhesive sheath, and wherein step (c) of removing the protective layer from the resilient adhesive sheath to expose at least a portion of the adhesive layer comprises gripping of the projecting element.

17. The method of claim 10, wherein the protective layer is formed of an elastically deformable material, and wherein during step (b) of the transitioning the resilient adhesive sheath to the expanded configuration, the protective layer is configured to elastically deform so as to remain disposed over the adhesive layer.

18. The method of claim 10, wherein the protective layer is not formed of an elastically deformable material, and wherein during step (b) of the transitioning the resilient adhesive sheath to the expanded configuration, the protective layer is configured to remain disposed over the adhesive layer without elastically deforming.

19. The method of claim 10, wherein step (c) of removing the protective layer from the resilient adhesive sheath to expose at least a portion of the adhesive layer comprises detaching the protective layer from resilient adhesive sheath according to a helical procession.

* * * * *